(12) United States Patent
Gevaert et al.

(10) Patent No.: US 7,118,909 B2
(45) Date of Patent: Oct. 10, 2006

(54) APPARATUS AND METHOD FOR BIOMATERIAL ASSAY

(76) Inventors: Matthew R. Gevaert, P. O. Box 44, Central, SC (US) 29630-0044; Karen J. L. Burg, 125 Knollwood Dr., Clemson, SC (US) 29631

( * ) Notice: Subject to any disclaimer, the term of this patent is extended or adjusted under 35 U.S.C. 154(b) by 250 days.

(21) Appl. No.: 10/146,683

(22) Filed: May 15, 2002

(65) Prior Publication Data

US 2002/0182720 A1    Dec. 5, 2002

Related U.S. Application Data

(60) Provisional application No. 60/294,536, filed on May 30, 2001.

(51) Int. Cl.
*C12M 3/00* (2006.01)
*C12M 1/20* (2006.01)

(52) U.S. Cl. .............. 435/288.4; 435/297.5; 435/305.3; 422/102

(58) Field of Classification Search .......... 435/29, 435/30, 32, 33, 288.3–288.5, 297.1, 297.2, 435/297.5, 305.1–305.4; 422/101, 102; 403/193, 403/194, 201, 238, 240, 245, 246, 263, 264, 403/364; 285/124.3, 124.5, 140.1, 189, 194, 285/200, 221, 202, 330, 382.1, 382.2, 382.4, 285/399; 248/56
See application file for complete search history.

(56) References Cited

U.S. PATENT DOCUMENTS

| | | | | |
|---|---|---|---|---|
| 3,580,988 | A | * | 5/1971 | Orlowski et al. ....... 174/153 G |
| 3,591,480 | A | * | 7/1971 | Neff et al. ............. 204/403.11 |
| 4,686,190 | A | * | 8/1987 | Cramer et al. ........... 435/287.1 |
| 5,536,662 | A | * | 7/1996 | Humphries et al. ....... 435/287.1 |
| 5,801,055 | A | * | 9/1998 | Henderson ............... 435/297.5 |
| 6,027,694 | A | * | 2/2000 | Boulton et al. ............ 422/102 |
| 6,383,820 | B1 | * | 5/2002 | Bunn et al. ................. 436/518 |

FOREIGN PATENT DOCUMENTS

FR    2279016 A  *  3/1976

* cited by examiner

*Primary Examiner*—William H. Beisner
(74) *Attorney, Agent, or Firm*—Stephen R. Chapman

(57) ABSTRACT

An apparatus to facilitate precise and efficient evaluation of biomaterials using direct contact cell culture techniques. The apparatus positions the biomaterial and creates the potential to form a fluid-tight seal between the biomaterial and the apparatus, at which point the biomaterial is exposed to cells and/or media. An assay method based on the apparatus is claimed.

3 Claims, 10 Drawing Sheets

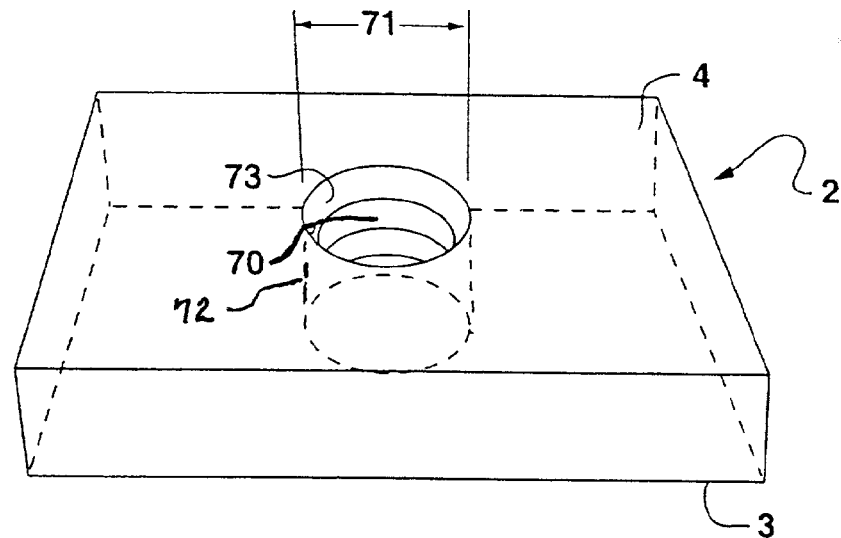
FIG. 7A
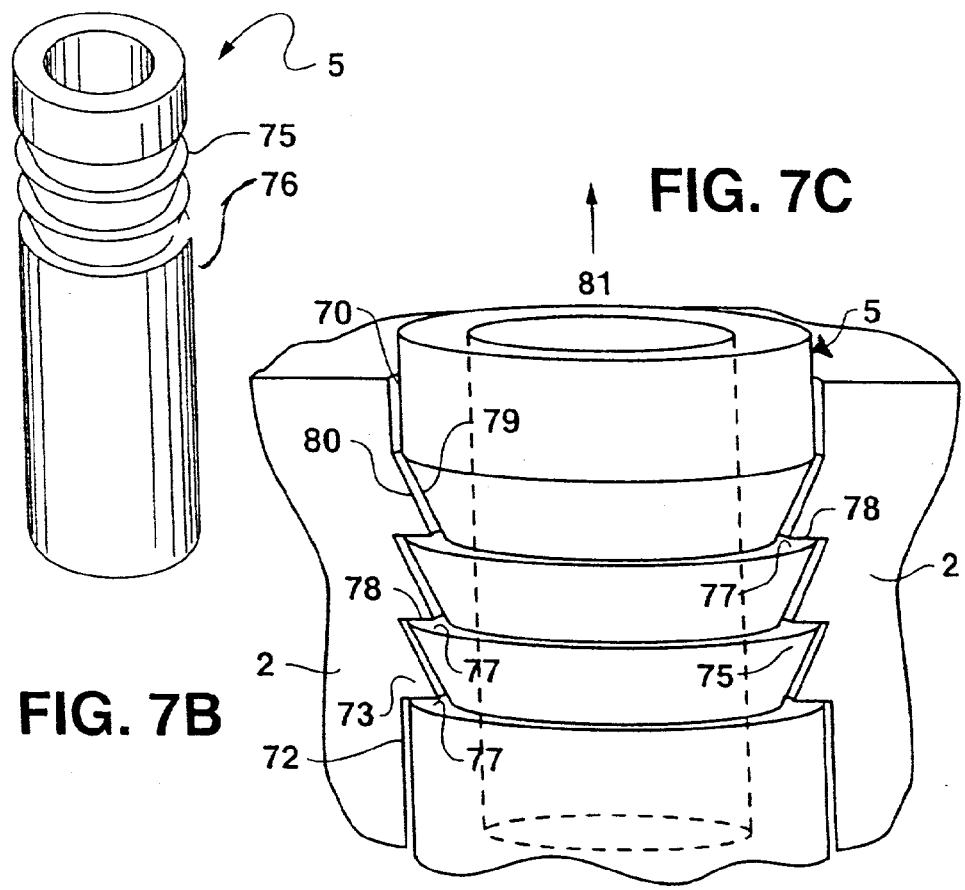
FIG. 7B
FIG. 7C

APPARATUS AND METHOD FOR BIOMATERIAL ASSAY

RELATED APPLICATIONS

This application claims the benefit of U.S. Provisional Patent Application No. 60/294,536 filed May 30, 2001 and which is incorporated herein by reference.

BACKGROUND OF THE INVENTION

1. Field of the Invention

This invention is directed towards a laboratory device that facilitates studies using cell culture techniques to assay biomaterials. Specifically this invention is a device that facilitates control of the exposure of animal cells and/or media to biomaterials and the measure of the main and interaction effects of the cells, tissue and media on the biomaterials. By way of example, but not as a limitation, the device can be used to evaluate biomaterial toxicity or drug release from films. The laboratory device also facilitates the recovery of biomaterials, cells, tissues, and/or the cell-material interface following controlled experiments.

2. Background

Technology related to the continued development of medical devices for humans comprises two fundamental areas of research and development: design and fabrication of said devices and development of minimally toxic, biologically compatible materials (biomaterials) to be used in the manufacture of said medical devices. Safety and health considerations require that the potential of toxic effects of biomaterials that are otherwise suitable for medical devices must be fully evaluated, and performance considerations require that the material maintain its function in an in vivo environment. Devices to facilitate cell culture and study are known in the art as shown and claimed in U.S. Pat. Nos. 5,578,492 and 5,139,951, which are hereby incorporated by reference in their entirety.

Direct contact cell culture is employed to evaluate biomaterial reactions and interaction of cells with a biomaterial. Evaluation includes toxicity, drug delivery, or material degradation analysis. Such studies require a laboratory apparatus that supports cellular growth, allows cell cultures to be exposed to known amounts of biomaterials, and to be handled for study purposes which includes observation of cells, sampling materials and media, changing media, and moving samples into and out of controlled environment facilities while protecting samples from contamination. Additionally, such evaluation apparatuses must provide a container which provides surfaces to support cellular growth.

Details of the preparation of media and methods of culture of cells are well known and comprehended by those skilled in the art. Specific environmental conditions including factors such as minimizing contamination of cultures and maintaining controlled temperature, humidity, and light conditions are common to all studies although specific conditions of light, temperature, and humidity may vary with the material to be tested. Nonetheless, the specific conditions are well known to those skilled in the art or are otherwise readily available without the need for excessive experimentation. See for example, R. I. Freshney, "Culture of Animal Cells", $2^{nd}$ ed., Wiley/Liss, 1994, N.Y., N.Y., which is hereby incorporated by reference in its entirety.

With current technology, biomaterials may float or otherwise move during the study making precise observations more difficult. To minimize these issues, materials are commonly glued or weighted, which introduces additional complications. Additionally, current technology necessitates mechanical collection using a spatula or similar instrument to recover the cells from bioassay apparatus. Commonly, this results in damage to the cells thereby reducing the value of the cells for further analysis. These and related difficulties limit aspects of the accuracy and dependability of biomaterial assays. Accordingly, there remains room for variation and improvement in the art.

SUMMARY OF THE INVENTION

It is an object of the present invention to provide a biomaterial assay apparatus and process which provides a stable, controlled surface for cell growth and study. Further the apparatus and process may expose the cells to only a single surface of the biomaterial. The fixed positioning of the biomaterial being evaluated minimizes damages to cell material and resultant experimental error. In addition, the apparatus is readily manufactured using injection-molding techniques as would be recognized by one skilled in the art.

This and other objects of the invention are accomplished by a well-plate insert comprising a support platform and at least one cylinder that traverses and is connected to the platform. A portion of the cylinder extends below the platform and fits into a well of a multi-well plate. The distal end of the extended portion of the cylinder contacts the floor of the well and is capable of forming a fluid-tight seal with a biomaterial placed on the floor. The well-plate is positioned in a frame connected to the platform of the sleeve insert. The connection can be adjusted to increase a compressible force between the interface of the cylinder and biomaterial, thereby creating the potential for a fluid-tight seal between the biomaterial and cylinder and simultaneously preventing excessive movement of the biomaterial to be assayed. In this configuration, only a specified portion of the biomaterial is exposed to cell growth, and cells are protected from damage.

Further, the invention includes a process for the assay of biomaterial, for using the growth of animal cells on the biomaterial as a bio-indicator of toxicity of the biomaterial. The process requires providing a container suitable for cell culture and placing a substantially flat sample of biomaterial on the floor of the container, followed by inserting a hollow, open-ended cylinder into the container with the distal end of the cylinder over and contacting the biomaterial throughout its full circumference. These steps are followed by applying compressible pressure on the cylinder thereby allowing a fluid-tight seal between the cylinder and biomaterial, followed by introducing animal cells and appropriate, supporting growth media to the cylinder and contacting the biomaterial with the cells and media, and next culturing the cells, followed by assaying the cells, and finally recovering the sample of biomaterial for additional study, assays, and observations.

BRIEF DESCRIPTION OF THE FIGURES

FIG. 7A illustrates a modified platform to accommodate a moveable cylinder.

FIG. 7B provides illustrates modifications of a cylinder to permit unidirectional movement in a modified platform.

FIG. 7C illustrates interlocking surface of the platform and cylinder.

DETAILED DESCRIPTION OF THE PREFERRED EMBODIMENT

Detailed Description of the Figures

Figure 1:
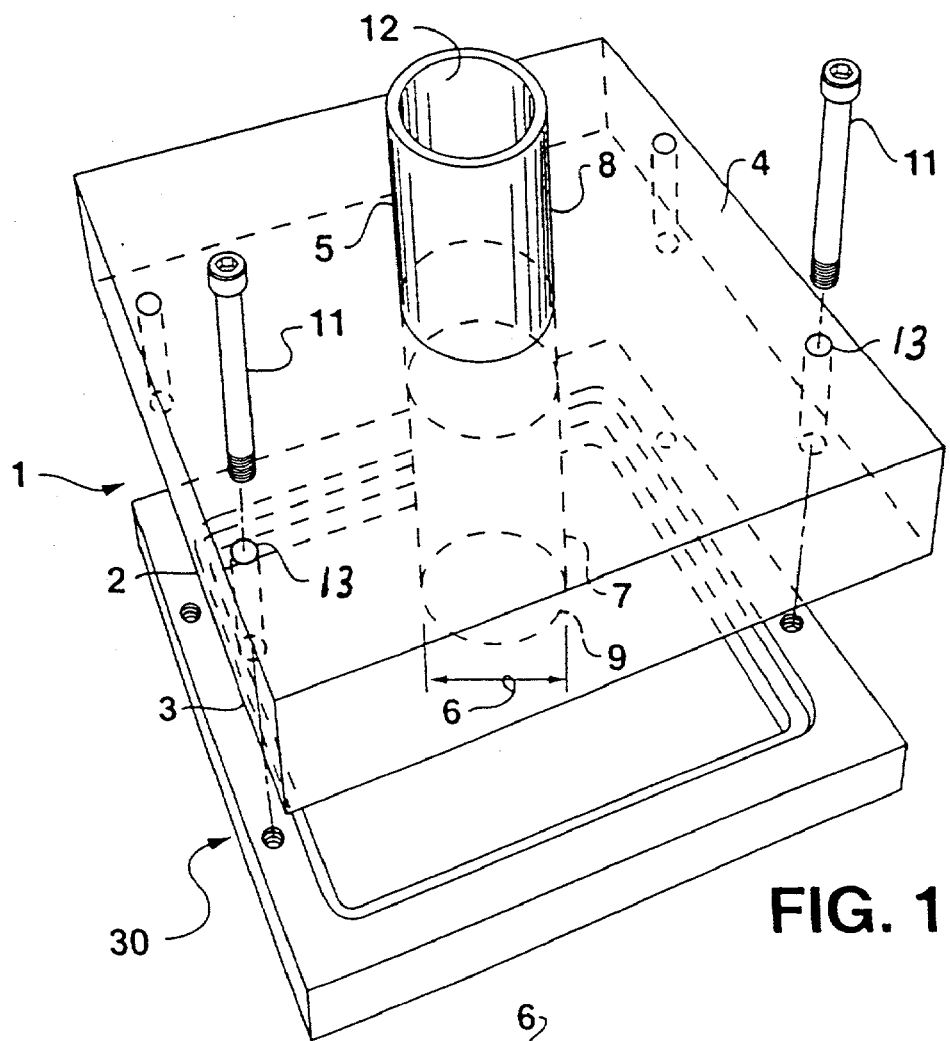
FIG. 1 illustrates the well plate insert.

FIG. 1 illustrates a well plate insert 1 with a platform 2 with a bottom surface 3, a top surface 4, a cylinder 5, with an open longitudinal core traversing the platform 2 from the top surface 4 to the bottom surface 3, and the cylinder 5 having a lower portion 7 extending below the platform 2, a distal end 9, a proximal end 8 and an outside diameter 6. Apertures 13 are positioned for connectors 11 to physically connect the platform to the base 30. The cylinder 5 traverses the platform 2 and is either molded as part of the platform 2 or secured to an aperture traversing the platform 2 (aperture not illustrated).

Figure 2:
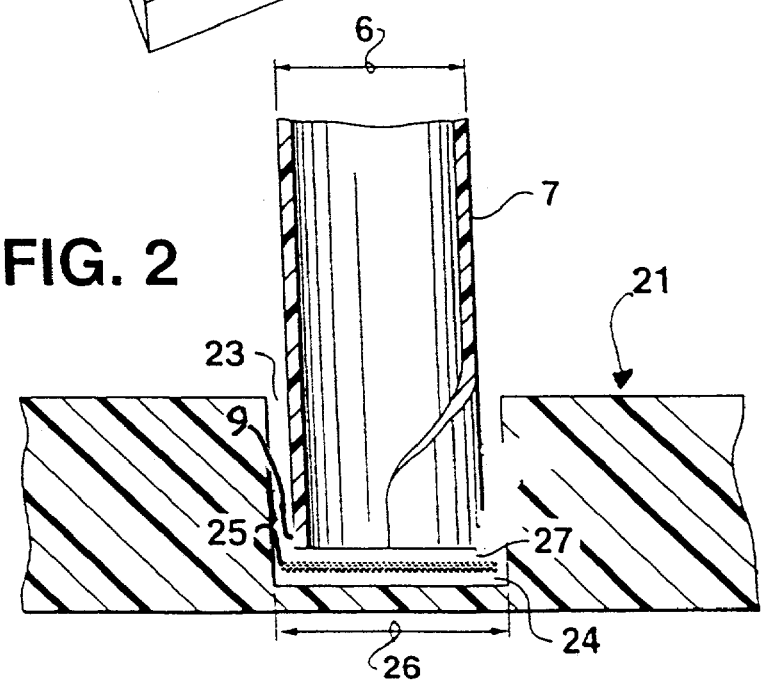
FIG. 2 provides a cross-section view of a well plate and its relationship to the biomaterial and cylinder.

FIG. 2 describes the spatial relationship of the lower portion of the cylinder 7, the well-plate 21 with well 23 having a sample of biomaterial 25 positioned on the floor 24 of well 23. The outer diameter 6 of the lower portion of the cylinder 7 is less than the diameter of the well 26 such that the the lower portion of the cylinder 7 can be inserted into the well 23 with the distal end of the cylinder 9 contacting the biomaterial 25 and creating the potential to form a fluid-tight seal at the point of contact 27.

Figure 3:
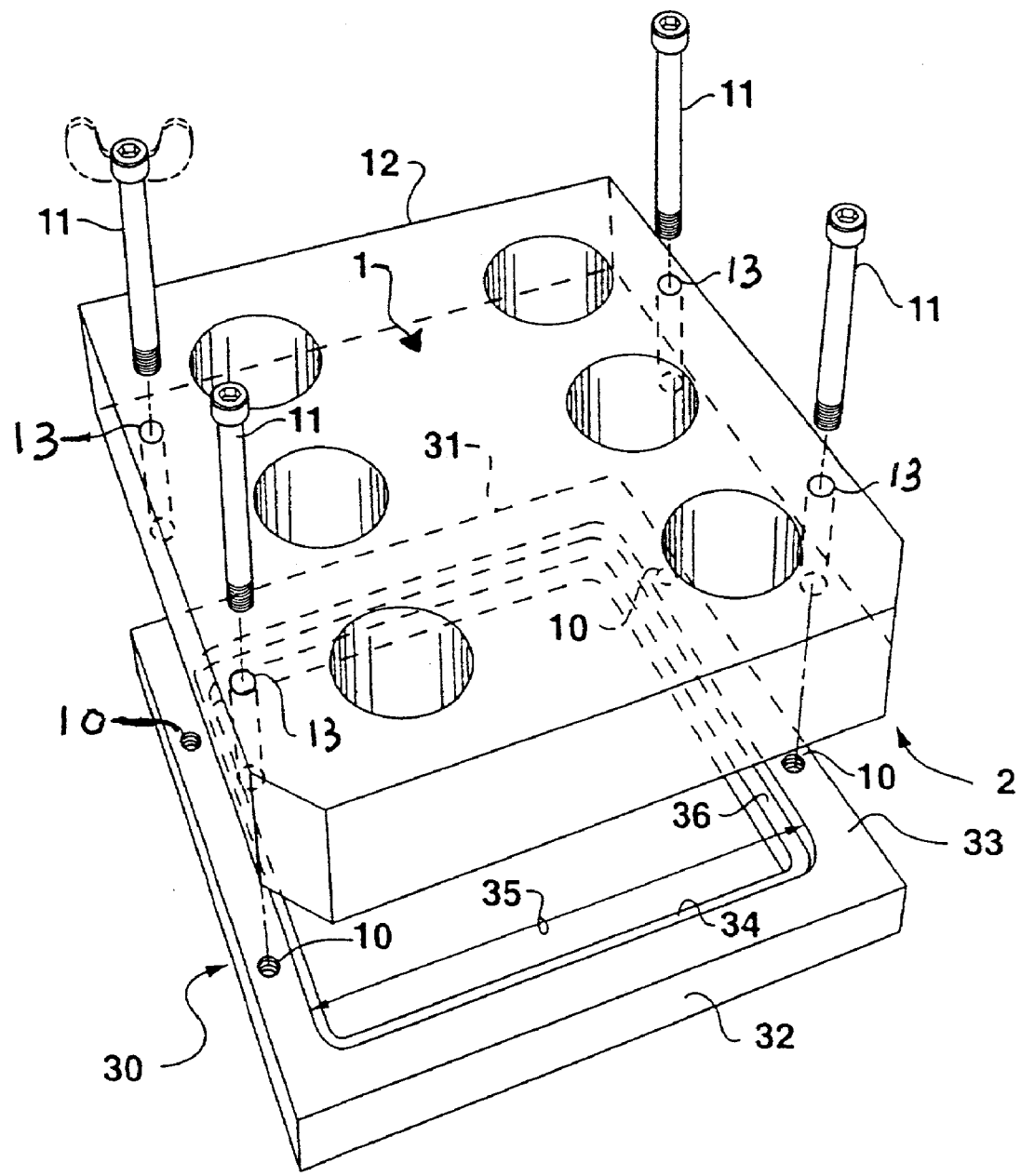
FIG. 3 illustrates the base that supports the well plate and is connected to the sleeve insert.

FIG. 3 describes a rectangular base 30 capable of supporting a multi-well plate (as illustrated in FIG. 2) and of being connected to the platform 2 of the well plate insert 1 by means of threaded connectors 11. The base 30 comprises a back piece 31, a front piece 32, and side pieces 33. A ledge 34 is created by a groove on the interior of the front, side, and back pieces. The width 35 and length 36 of the ledge are determined by the corresponding dimensions of the well plate to be supported. Threaded apertures 10 are defined by the edge of the base, and positioned to align precisely with corresponding apertures 13 in the platform 2 to receive threaded connectors 11.

Figure 4:
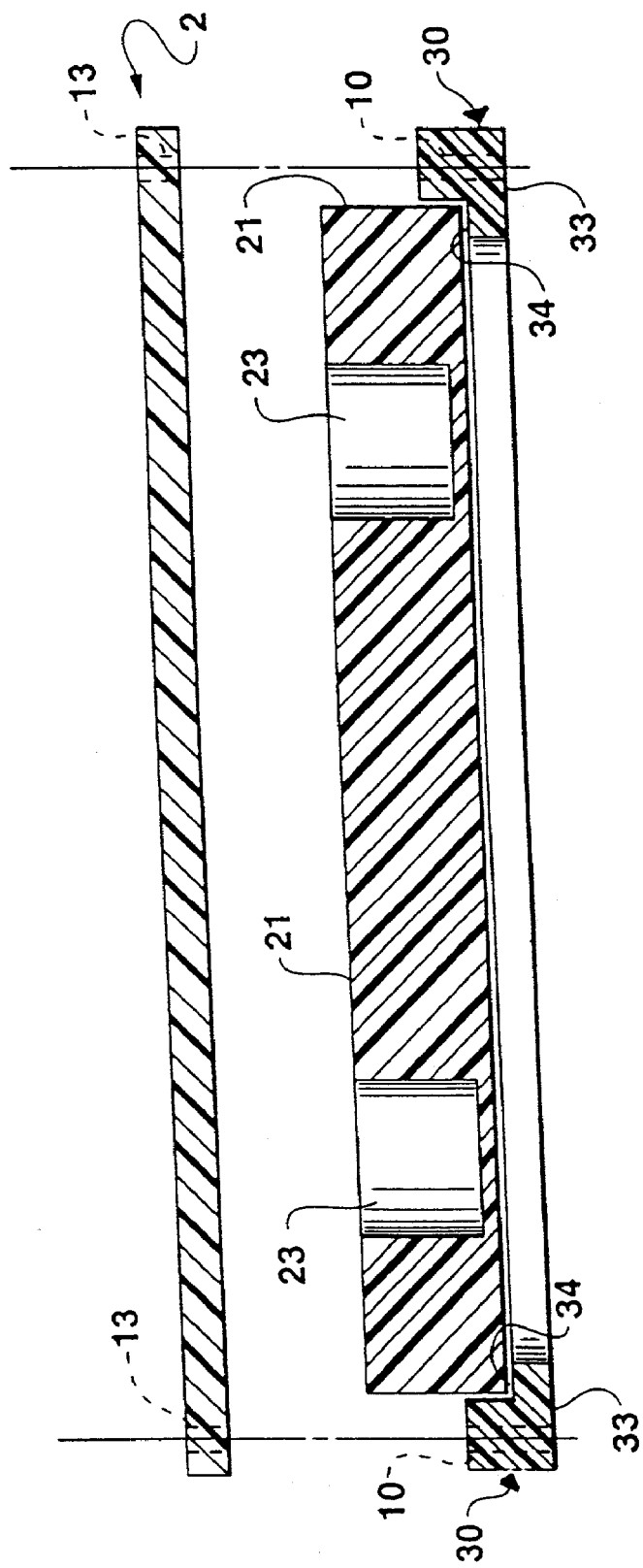
FIG. 4 provides a cross-section diagram of a well plate positioned in and supported by the base.

FIG. 4 illustrates a cross-section of the base 30 with a well-plate 21. Well-plate 21, including wells 23, is illustrated here positioned on ledge 34 formed on sidewalls 33 of base 30. Threaded apertures 10 are positioned to correspond to and align with apertures 13 of the platform 2.

Figure 5:
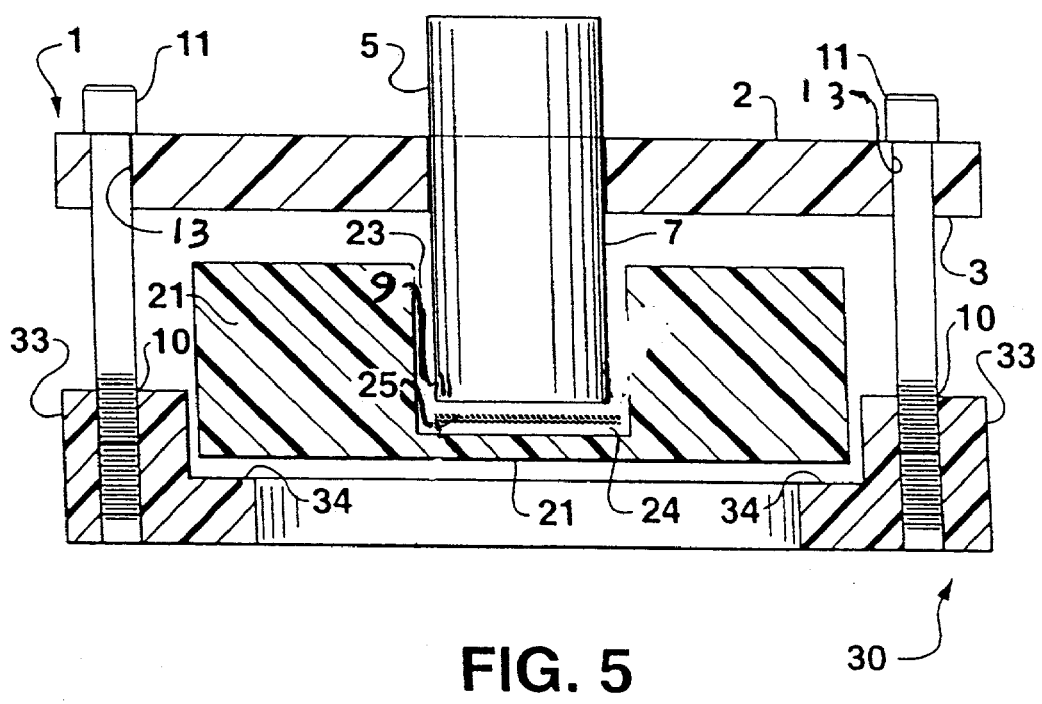
FIG. 5 is a cross-section illustration of the platform connected to the base and the relationship of the well-plate insert, platform, cylinders, and connectors

FIG. 5 illustrates in cross-section the spatial and functional relation of the components. Well plate 21 is positioned on ledge 34 of side wall 33 of base 30. Cylinder 5 is connected to platform 2 with lower portion of cylinder 7 extending below bottom surface of platform 3. Biomaterial 25 is positioned on floor of well 24. Distal end 9 of cylinder 5 is inserted in well 23 and contacts biomaterial 25. Apertures 13 in platform 2 and threaded apertures 10 in base 30 align such that connectors 11 physically connect platform 2 and base 30. Tightening connectors 11 creates the potential of a fluid-tight seal at the distal end of the cylinder 9, between the biomaterial 25 and cylinder 5 by bringing well plate insert 1 relatively closer to base 30 thereby producing a compressive force on the interface 27 of the distal end 9 of the cylinder 5 and the biomaterial 25.

Figure 6A:
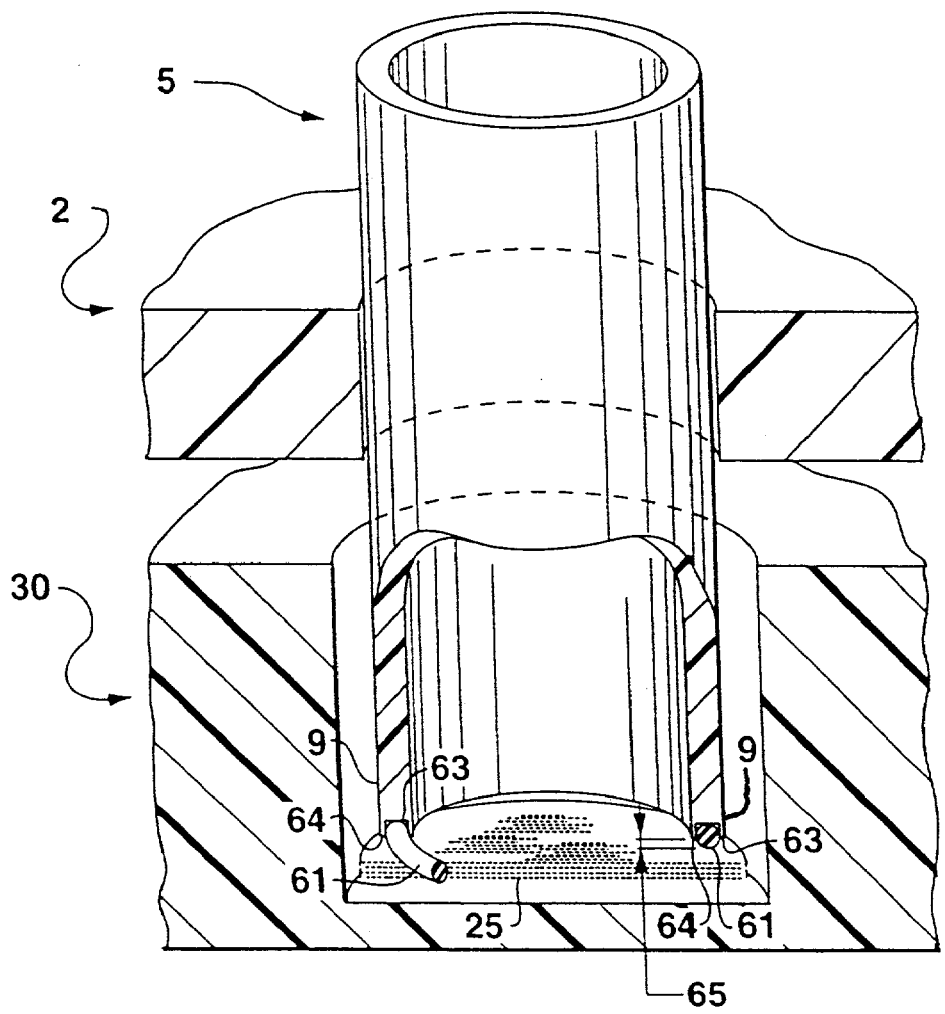
FIG. 6A illustrates adaptation of the cylinder to facilitate sealing biomaterial disks with a compressible O-ring positioned in the distal end of the cylinder.

FIG. 6A illustrates a longitudinal cross section of the cylinder 5 adapted to position and hold a compressible gasket or O-ring 61 on the distal end of the cylinder 9. A groove 63 to receive the O-ring 61 is formed in the distal end face of the cylinder 64. The O-ring 61 fits into the groove 63 with approximately one-half of its thickness 65 exposed to form a seal with the biomaterial 25. This creates the potential to form a fluid-tight seal between the O-ring 61 and biomaterial 25 when compressed as a result of the compressive connection joining platform 2 and base 30.

Figure 6B:
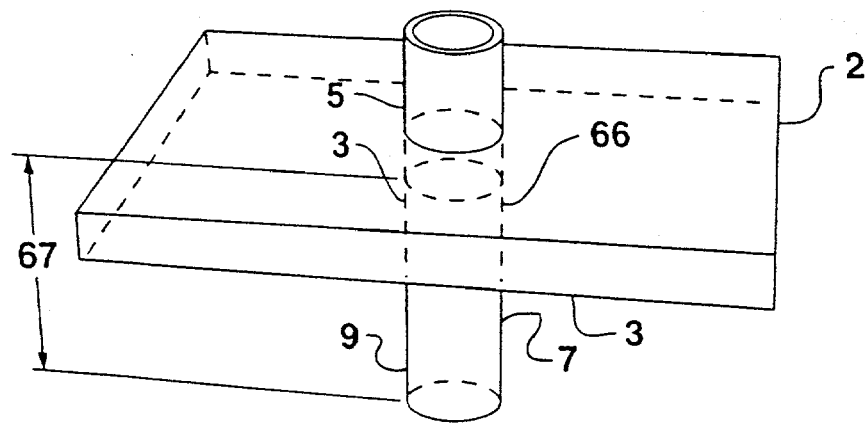
FIG. 6B illustrates an alternative adaptation to sealing biomaterials of different thicknesses by fabricating a portion of the cylinder with a compressible material, such as rubber.

FIG. 6B illustrates the position of a compressible material as a segment of the lower portion of the cylinder 7. Cylinder 5 traverses platform 2, and lower portion of cylinder 7 extends below the bottom surface of the platform 3. Any portion of the length 67 of the lower portion of cylinder 7 starting at point 66 of the lower portion of the cylinder 7 and extending towards the distal end of the cylinder 9 may be fabricated from a compressible material such as, but not limited to rubber. This portion 67 serves essentially the same function as the previously described function of O-ring 61.

FIG. 7A describes a modification of the platform 2 in which an opening 70 with a diameter 71 traverses the platform 2 from its top surface 4 through its bottom surface 3. Opening 70 is defined by a wall 72 with horizontal, uniformly spaced ridges 73 formed on the surface of the wall 72. One skilled in the art would recognize that, alternatively, the ridges 73 may be formed and characterized as threads.

FIG. 7B describes modifications of cylinder 5 that permits only unidirectional movement of cylinder 5 through opening 70 in platform 2. Uniformly spaced, horizontally parallel ridges 75 are formed over at least a portion of the outer surface 76 of the cylinder 5. The ridges 75 are spaced and shaped to permit cylinder 5 to be inserted at the top surface 4 of platform 2 and to move downward. The configuration prevents opposite movement. One skilled in the art would recognize that, alternatively, the ridges 75 may be formed and characterized as threads that circumscribe the outer surface of the cylinder 76. The threads are adapted to receive threads formed on the surface of wall 72. In this configuration, the cylinder may be moved upward or downward by reversing the rotation of the cylinder as it is inserted in opening 70.

FIG. 7C details how relative movement of the cylinder 5 through opening 70 is restricted. When cylinder 5 is inserted in opening 70, the flat surface 77 of ridge 75 formed on cylinder 5 contacts the corresponding flat surface 78 of ridge 73 formed on wall 72 of opening 70 in platform 2. Opposing flat surfaces resist upward pressure, arrow 81, of the cylinder 5 in relation to platform 2. Corresponding beveled surfaces on the cylinder 79 and beveled surfaces on the platform 80 will allow downward movement of cylinder 5 through opening 70 in platform 2. Thus, when platform is physically linked to base, and cylinder is inserted into a well, downward pressure relative to platform on cylinder can create a fluid-tight seal to be maintained between the distal end of the cylinder and biomaterial positioned on the floor of the well.

Figure 8:
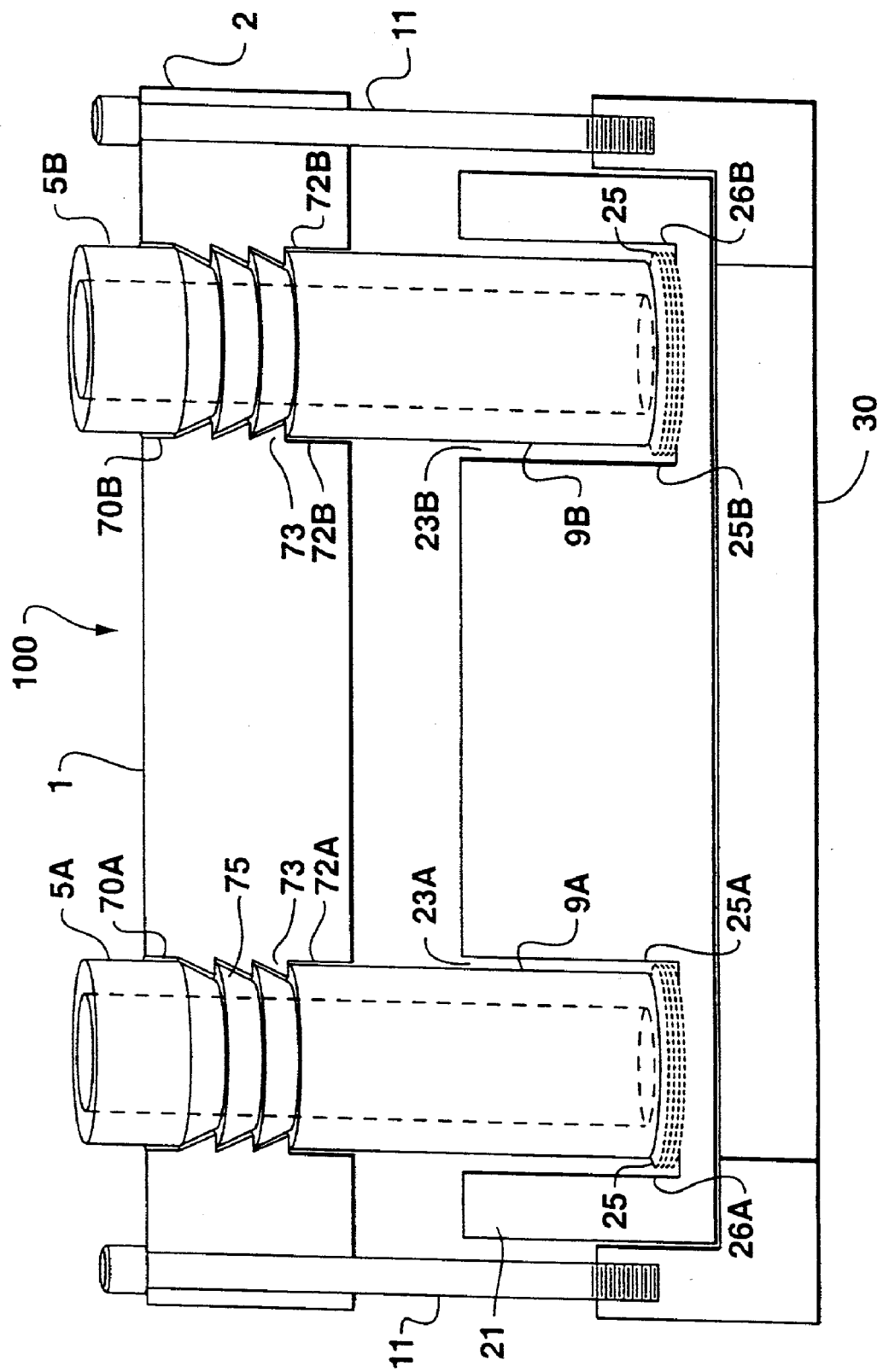
FIG. 8 illustrates adaptation of bioassay apparatus to biomaterials of different thicknesses.

FIG. 8 illustrates cylinders 5A and 5B traversing corresponding openings 70A and 70B in platform 2. Distal ends 9A and 9B of corresponding cylinders are inserted into corresponding wells 23A and 23B of multi-well plate 21. Platform 2 is connected to base 30 by connectors 11. Samples of biomaterial 25A and 25B of different thicknesses are positioned in corresponding wells 23A and 23B. Interlocking ridges 73 and 75 formed on the adjacent, opposing surfaces of cylinders 5A and 5B and corresponding wall of opening 72A and 72B allow cylinders to be pressed downward so that contact is made with biomaterial samples. Biomaterial sample 25B for illustrative purposes is thicker than biomaterial sample 25A.

Figure 9:
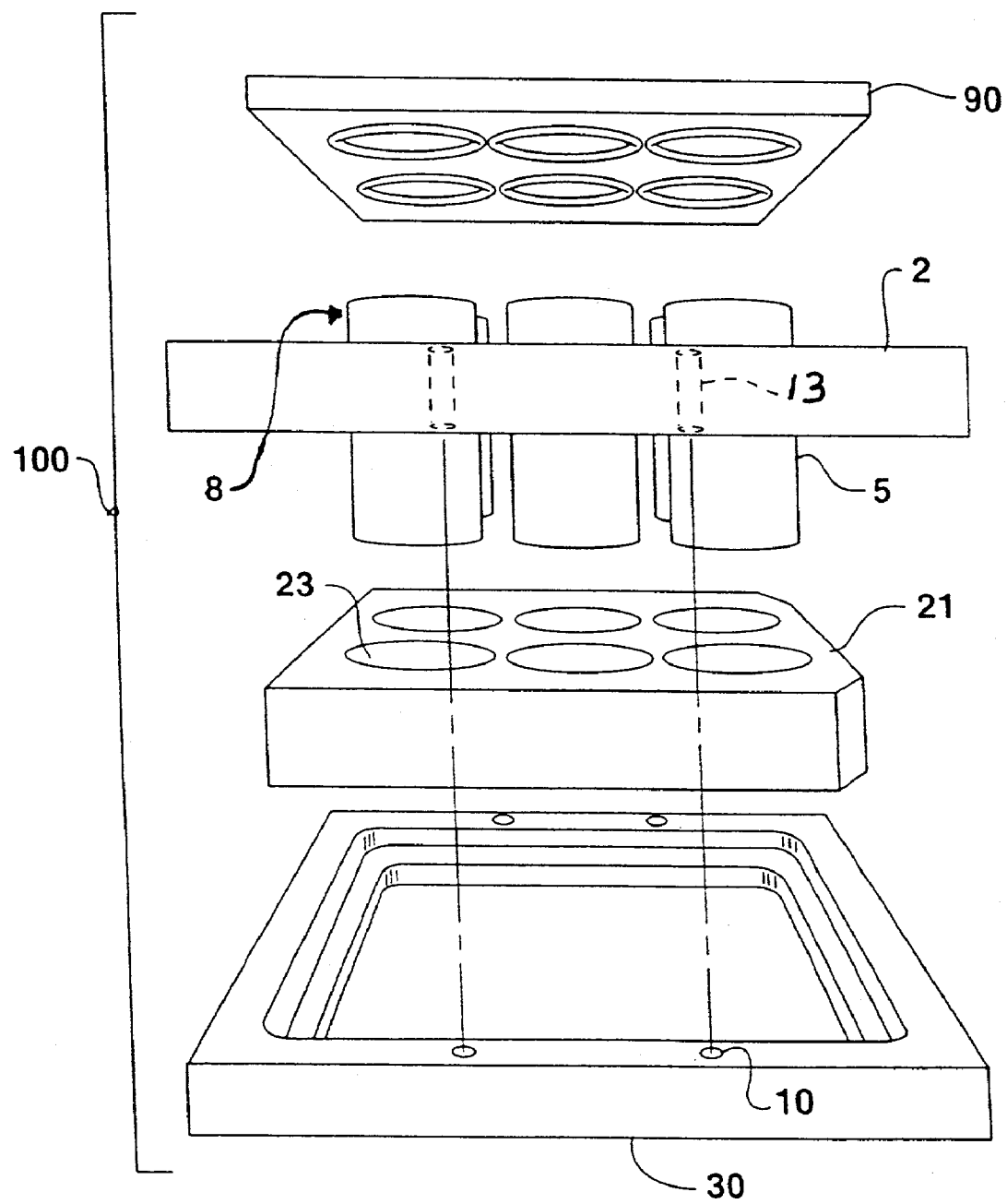
FIG. 9 illustrates the four major elements of a bioassay apparatus.

FIG. 9 illustrates the four basic elements of a bioassay apparatus 100. When assembled the units are stacked in a nested configuration. Base unit 30 serves as a rectangular frame capable of supporting multi-well cell plate 21. By way of illustration, but not limitation, multi-well cell plate 21 comprises six wells 23. The well plate insert comprises one or more cylinders 5 that traverse a platform 2 and are structurally attached to the platform. Edges of the platform further define a plurality of apertures 13. Lid unit 90 rests on and covers the proximal ends 8 of the cylinders 5.

Figure 10:
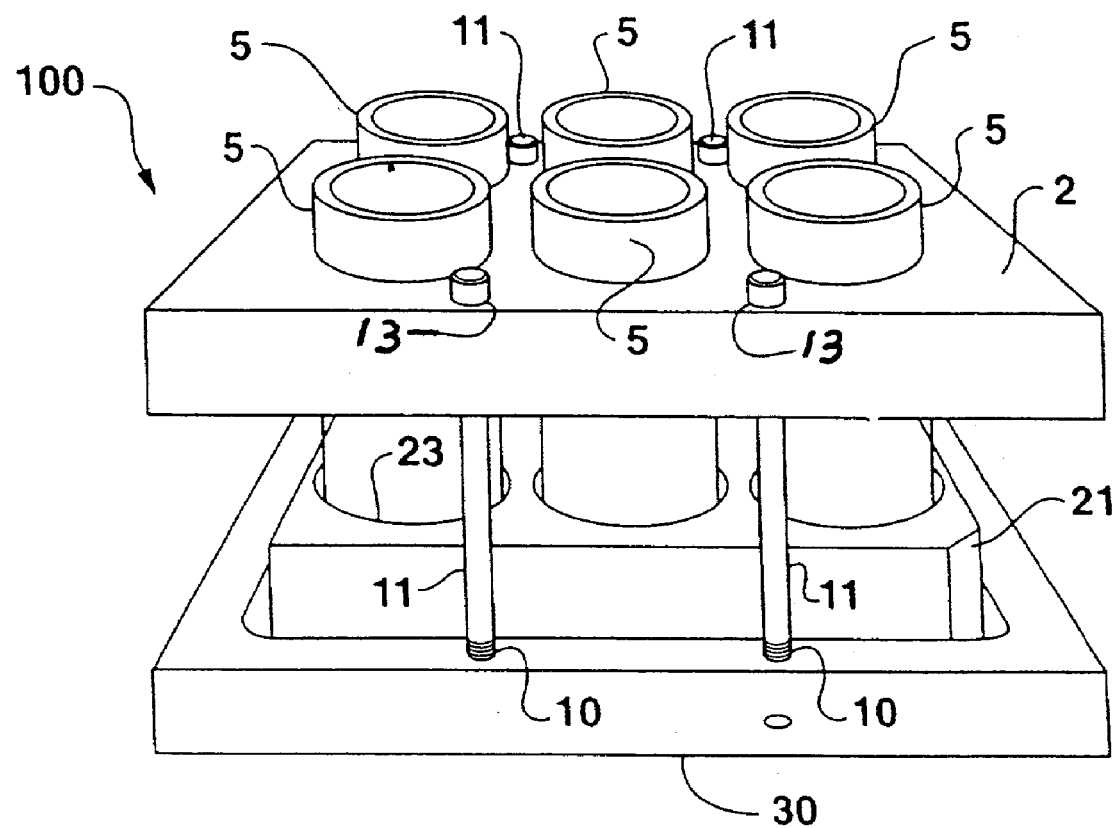
FIG. 10 provides an angular top view of the nested bioassay apparatus.

FIG. 10 describes and illustrates the relationship of the elements of a bioassay apparatus 100 from the perspective of an angular top. Multi-well plate 21 is nested into base 30. Distal ends (illustrated as 9 in FIG. 1) of plurality of cylinders 5 are inserted into wells 23 of well plate 21. Connectors 11 are inserted through apertures 13 and are threaded into threaded apertures 10 and tightening connectors 11 creates a compressive force at point of contact 27 of cylinder 5 and biomaterial 25. Lid unit 90 fits over the proximal ends of cylinders (illustrated as 8 in FIG. 1) and fits nest fashion on platform 2.

Figure 11:
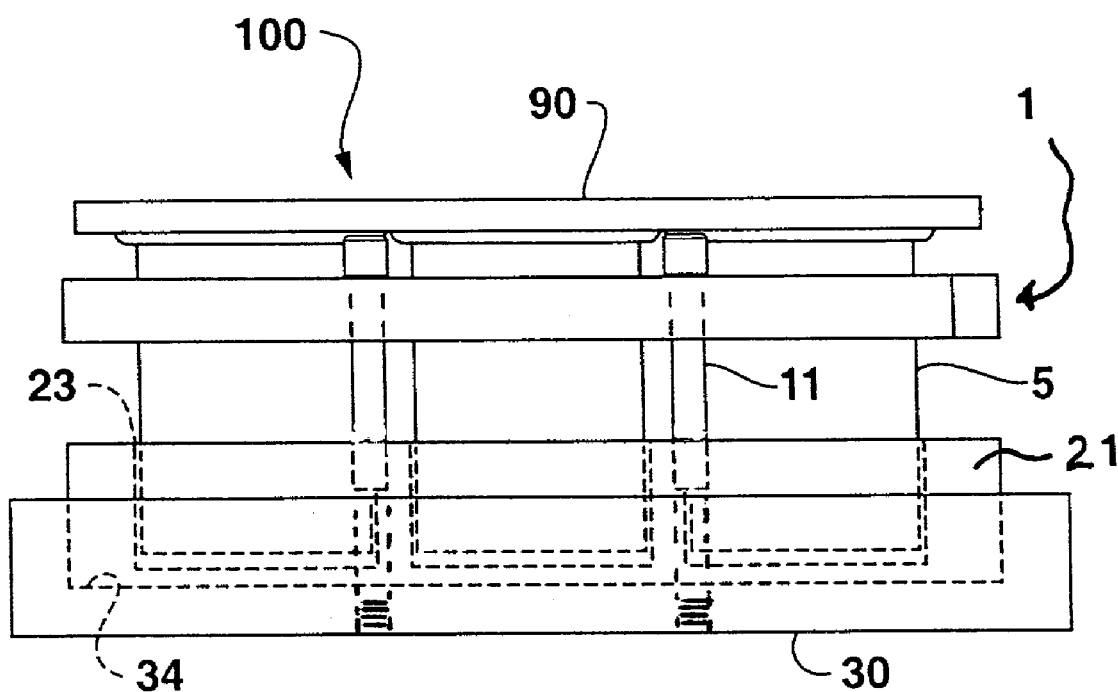
FIG. 11 provides a front view of the nested bioassay apparatus.

FIG. 11 provides a face on view of bioassay apparatus 100. Multi-well plate 21 is positioned on ledge 34 formed by groove in base 30. Well plate insert 1 is positioned above multi-well plate 21 with cylinders 5 inserted into wells 23. Connectors 11 are fully tightened producing a compressive force at interface of distal end of cylinder and biomaterial positioned on floor of well 23.

EXAMPLE I

As seen in reference to FIG. 9, the major elements of a bioassay apparatus 100 are the base 30, a multi-well plate 21 with a plurality of wells 23, a well plate insert 1 comprising a plurality of open ended, hollow cylinders 5 attached to a platform 2, and a lid 90. Details of these elements and their spatial and functional relationships are described in the following example and discussion of certain figures.

As seen in reference to FIG. 3, a base 30 is provided which may be in the form of a rectangular frame. An outer margin of the frame can define a plurality of threaded apertures 10. An upper surface of the base defines a ledge 34 formed by a notch or groove which further defines a receiving surface for a conventional multi-well plate 21 (as illustrated in FIG. 2).

As seen in reference again to FIG. 9, multi-well plate 21 may be provided by a conventional six-well plate as are commercially available from, for example Fisher Scientific, Pittsburgh, Pa. 15275. While the illustrated embodiment provides for a six-well plate, the number, size, and spacing of the individual wells can vary. The ledge 34 on the interior of the base 30 is adapted for nesting with the lower rim of the multi-well plate 21.

As seen by FIG. 5 which represents the detail of only one of a plurality of wells 23 and associated elements of the assay apparatus, open-ended, hollow cylinder 5 traverses the platform 2 of the well plate insert 1. Cylinder 5 is formed as part of, or attached to platform 2. A lower portion 7 of cylinder 5 extends below the bottom surface of the platform 2. The proximal end 8 (as illustrated in FIG. 1) of the cylinder 5 extends above the top surface of the platform 2. Thus each of the plurality of cylinders 5 corresponds to one well 23 of the plurality of wells in a multi-well plate 21, and the cylinder 5 allows access via the proximal end 8 of the cylinder 5 through the platform 2 to the distal end 9 of the cylinder 5. The bottom edges of the multi-well plate 21 are nested within the groove of the corresponding edge of the base resting on and supported by the ledge 34. A sample of biomaterial 25 is positioned on the floor of a well. The distal end 9 of the cylinder 5 is inserted into the well 23 and contacts the biomaterial 25. Both the well-plate insert 1 and the base 30 further define a plurality of threaded apertures 10 which are vertically aligned when cylinders 5 are inserted into corresponding wells 23 in the multi-well plate 21 positioned on the base 30, and the bioassay apparatus 100 (as illustrated in FIG. 9) is in a stacked configuration. Threaded connectors 11 inserted through the apertures 13 and 10 connect the well plate insert 1 and base 30 and provide a means of exerting a compressive force between these elements by tightening the connectors 11. It is to be noted that FIG. 5 represents and illustrates only a single cylinder-well association in a cross-section view from the front of a bioassay apparatus 100. Reference to FIG. 9 illustrates a configuration with six wells 23, by means of example, not limitation.

As seen in reference to FIG. 9, a lid 90 is provided having an upper surface and a lower surface. A lower surface of the lid 90 is surrounded by a protruding flange which extends around the perimeter of the lid 90. As seen in further reference to FIG. 10, the lid has a similar size and shape to the platform 2, which is adapted to engage the lid 90. The inner surface of the lid 90 defines a plurality of circular ridges which correspond to the proximal ends 8 of each cylinder 5. For purposes of this invention, it has been found that a conventional lid 90 of commercially available multi-well plates 21 may be used. Fisher Scientific, Pittsburgh, Pa. 15275.

As best seen in reference to FIGS. 10 and 11, the assembled bioassay apparatus 100 uses the base 30 to engage a lower surface of a multi-well plate 21. Next, the well-plate insert 1 (as illustrated in FIG. 5) is positioned over the multi-well plate 21. As seen in the referenced figures, for each well 23 within the multi-well plate 21 a corresponding cylinder 5 can be provided and appropriately spaced so as to align each cylinder 5 with a corresponding well 23.

When so aligned, the apertures defined on the edges of the platform 2 (as illustrated in FIG. 5) and base 30 are aligned so as to receive a threaded connector 11 such as a bolt or screw. In this manner, the threaded connectors 11 can be used to apply a compressive force between the lower ends 7 of the cylinder 5 and the corresponding bottom portion of the multi-well plate 21. The lid 90 may then be placed over the top surface 4 of the platform 2, the lower surface of the lid 90 being in contact with at least the proximal end 8 of each cylinder 5, which extends above the upper surface of the platform 2.

As seen in reference to FIG. 5, the bioassay apparatus 100 can be used to test the compatibility of various biomaterials 25 as they are placed in contact with a test medium, which may contain living cells. For instance, a sheet of biomaterial 25 may be provided in which circular portions of a biomaterial 25 are cut and sized so as to be placed on the floor 24 of each well 23 of the multi-well plate 21. Thereafter, when the well-place insert 1 is brought into engagement with the multi-well plate 21, the engaging cylinder walls are placed in contact with the biomaterial 25. As seen in reference to FIG. 6A, a lower edge of each cylinder wall can support a corresponding "O" ring 61 or similar flexible gasket-like material. When the gasket material of the lower sleeve wall is brought in contact with the biomaterial, a seal, which may be fluid tight, results. The use of the threaded connectors 11 helps maintain the necessary compressive force between the cylinder 5 and the biomaterial 25 which may provide and maintain a fluid-tight seal. While threaded connectors are illustrated in the preferred embodiment, it is recognized that there are alternative means of supplying a suitable compressive force between the cylinder 5 and the biomaterial 25. For instance, spring-loaded clips could be used to secure the margins of the platform 2 to the base 30. Likewise, clamps or other tensioning devices may be used to supply the necessary compressive force.

For instance, by selecting the use of dense materials such as glass or dense plastics, the weight of the well-plate insert 1 could be sufficient to provide a necessary compressive force.

As is readily appreciated by one having ordinary skill in the art, the amount of compressive force that needs to be supplied would vary depending upon the presence of a gasket or other sealing material. Additionally, some biomaterials may have sufficient physical properties that a seal can be formed without the necessity of a separate gasket. In addition, it is recognized that depending upon the texture and surface features of the biomaterial being assayed, a rough or textured material may require a more specialized gasket and/or increased compressive forces to bring about an effective seal. In specific cases a seal is not necessary or will not be possible. In these cases the insert will simply position the material.

Once a seal has been established, a test medium, for example a population of cells and growth media may be introduced through the upper opening defining each cylinder and brought into contact with the biomaterial. In this manner, the biomaterial is maintained in intimate contact with the growth media and resident population of cells. The biomaterial is firmly held in place by the compressive forces of the cylinder walls. Accordingly, the biomaterial is immobilized which eliminates cell damage attributed to movement of the biomaterial.

The above described embodiment is preferred in that it makes use of conventional and readily available multi-well assay plates. However, the process of carrying out the biomaterial assay can employ a variety of different apparatuses. For instance, a base unit may be provided in which a flat sheet of biomaterial is placed. A hollow cylinder-like structure may thereafter be brought into contact with the biomaterial so as to bring about a fluid-tight seal between the biomaterial and the engaging cylinder surface. An upper opening in the cylinder can provide an entry way for the addition of a cell culture and growth media. In this arrangement, a conventional assay plate is not needed in that the hollow cylinder is used to define an enclosure relative to the biomaterial which can contain the cells and media.

The entire device may be made of any materials that tolerate sterilization. In a preferred embodiment, the material is polystyrene. The invention anticipates a variety of materials including, but not limited to, appropriate polymers, glass, and metals.

EXAMPLE II

As seen by reference to FIG. 8, illustrating a well plate 21 with two wells 23, the current invention may be adapted for the study of biomaterials 25 of significantly different thickness. The number of wells 23 is for illustration purposes and not as a limitation. As seen by reference to FIG. 7A, a cylinder 5 adapted with closely spaced ridges, teeth, or serrations 75 in horizontally parallel arrangement along part of its exterior surface. Reference to FIG. 7B illustrates corresponding structures. The serrations 75 circumscribing the walls 72 define an aperture 70 in the platform 2. Reference to FIG. 7C illustrates how a cylinder 5 inserted into the aperture 70 moves downward, but the shape and structure of the serrations 75 on the opposing surfaces of the aperture 70 and cylinder 5 for a locking interface that allows downward movement and restricts movement upward. The seal is created by tightening the connectors. Any previously described modification to the cylinder to enhance sealing may be incorporated into the cylinders employed in this example. This example requires the use of individual lids for each cylinder. Common types of commercially available laboratory petri dish lids have been found to be suitable. Fisher Scientific, Pittsburgh, Pa. 15275.

One of average skill in the art would recognize that the threads on the opposing faces of the cylinder and wall of the aperture in the platform could replace the serrations. In this configuration, the cylinder could be screwed into the aperture and depth adjusted in either an upward or downward direction. All other aspects of the invention remain as described, discussed and illustrated. In this configuration, the cylinder represents the male unit and the aperture the female unit. Regardless of the configuration, as can be inferred by reference to FIG. 7C, the sensitivity of the adjustment is a function of the space between serrations or the number of threads per centimeter of length of the cylinder or aperture.

EXAMPLE III

As seen in reference to FIG. 6B, a segment of the lower portion 7 of the cylinder 5 can be fabricated with a compressible material such as rubber. This adaptation serves the same function as the interlocking ridges and moveable cylinders, which is to accommodate biomaterials of different thicknesses. Thus, the modification described in FIG. 6B is appropriate for uses described in Examples I and II.

That which is claimed is:
1. A bioassay apparatus comprising:
a) a multi-well plate with at least one well, said well being defined by interior, vertical walls and a flat floor formed in a solid base unit;
b) a rectangular base having a top surface and a front, a back, and side members defined by edges, said multi-well plate positioned on said top surface;
c) a well-plate insert comprising a platform with a top surface, a bottom surface, and edges, said well-plate insert having at least one, open-ended, hollow cylinder, wherein said at least one, open-ended, hollow cylinder traverses said platform and is secured to said platform and said at least one, open-ended, hollow cylinder comprises a first length extending below said bottom surface of said platform, said first length terminating in a distal end, and said at least one, open-ended, hollow cylinder further comprises a second length extending above a top surface of said platform, and said second length terminating in a proximal end; and wherein said platform of said well-plate insert is physically joined to said rectangular base by mechanically adjustable connectors such that said distal end of said first length of said at least one, open-ended, hollow cylinder can contact a sample of biomaterial positioned on the floor of the at least one well of the said multi-well plate such that a fluid tight seal can be formed between said distal end of said first length of said at least one, open-ended, hollow cylinder and said floor of said at least one well formed in said multi-well plate; and d) a means to cover said proximal end of said second length of said at least one, open-ended, hollow cylinder, said means further being adapted to contact said edges of said platform when positioned to cover said proximal end.

2. The bioassay apparatus of claim 1, wherein said at least one, open-ended, hollow cylinder is secured to said platform by a plurality of first serrations and a plurality of second serrations, wherein said platform includes at least one aperture traversing said platform vertically from said top surface through said bottom surface, said at least one aperture being defined by an opening in said top surface and an opening in said bottom surface of said platform and by vertical walls, said vertical walls including said plurality of first serrations formed along at least a portion of the surface of said vertical walls and said plurality of first serrations include flat surfaces facing downwards towards said bottom surface of said platform, and wherein said at least one, open-ended, hollow cylinder includes an outer wall, said outer wall having said plurality of second serrations formed on at least part of its surface and said plurality of second serrations include flat surfaces facing opposite to said flat surfaces of said plurality of first serrations such that when said distal end of said at least one, open-ended, hollow cylinder is pressed into said aperture from said top surface it will move downwards, but resist upward movement by engaging the opposite facing flat surfaces of said plurality of first serrations on said vertical walls of said aperture.

3. The bioassay apparatus of claim 1, wherein said multi-well plate comprises from 2–96 wells.

* * * * *